United States Patent
Watts et al.

(10) Patent No.: US 8,137,289 B2
(45) Date of Patent: Mar. 20, 2012

(54) METHOD AND APPARATUS FOR OBTAINING ALIQUOT FROM LIQUID-BASED CYTOLOGICAL SAMPLE

(75) Inventors: Hal Watts, Holden, MA (US); Robert Sakal, Bolton, MA (US)

(73) Assignee: Cytyc Corporation, Marlborough, MA (US)

( * ) Notice: Subject to any disclaimer, the term of this patent is extended or adjusted under 35 U.S.C. 154(b) by 84 days.

(21) Appl. No.: 12/717,566

(22) Filed: Mar. 4, 2010

(65) Prior Publication Data
US 2010/0159584 A1  Jun. 24, 2010

Related U.S. Application Data

(62) Division of application No. 11/299,394, filed on Dec. 12, 2005, now Pat. No. 7,686,771.

(51) Int. Cl.
*A61B 5/00* (2006.01)
*G01N 1/00* (2006.01)
*G01N 1/12* (2006.01)

(52) U.S. Cl. .................. 600/573; 73/863.73; 73/864.63

(58) Field of Classification Search .................. 422/102; 435/288.2, 288.4, 288.5; 600/573; 73/863.73, 73/864.63
See application file for complete search history.

(56) References Cited

U.S. PATENT DOCUMENTS

| | | | |
|---|---|---|---|
| 416,435 | A | 12/1889 | Benner |
| 4,927,605 | A | 5/1990 | Dorn et al. |
| 5,425,921 | A | 6/1995 | Coakley et al. |
| 5,975,373 | A | 11/1999 | Forsberg |
| 6,277,646 | B1 | 8/2001 | Guirguis et al. |
| 6,393,926 | B1 | 5/2002 | Bowersox et al. |
| 6,509,164 | B1 | 1/2003 | Guirguis |
| 7,157,233 | B2 | 1/2007 | Fischer et al. |
| 2003/0059347 | A1 | 3/2003 | Ostgaard et al. |

(Continued)

FOREIGN PATENT DOCUMENTS

| WO | 03034035 | 4/2003 |
|---|---|---|
| WO | 2005014173 | 2/2005 |

OTHER PUBLICATIONS

PCT International Search Report and Written Opinion for PCT/US2006/061360, Applicant Cytyc Corporation, Forms PCT/ISA/210, 220 and 237, dated Aug. 2, 2007 (13 pages).

(Continued)

*Primary Examiner* — Max Hindenburg
*Assistant Examiner* — Adam Eiseman
(74) *Attorney, Agent, or Firm* — Vista IP Law Group LLP (57) ABSTRACT

Sample vials and methods of processing the sample vials are provided. The sample vial comprises a vial container, a sample collection chamber within the vial container, a vial cap configured to be mated with the vial container to enclose the collection chamber, an aliquot chamber, which may be carried by the vial cap or the vial container, and a valve mechanism for selectively sealing and unsealing the aliquot chamber from the collection chamber. The method may comprise flowing an aliquot of the sample from the collection chamber while the sample within the collection chamber is isolated from an environment exterior to the vial, sealing the aliquot chamber from the collection chamber to isolate the aliquot sample from the remaining sample portion, and transferring at least some of the remaining sample portion from the collection chamber to a microscope slide while the aliquot chamber is sealed from the collection chamber. The method further comprises reserving the slide for cytological screening of the sample, and reserving the aliquot sample for deoxynucleic acid (DNA) testing.

11 Claims, 6 Drawing Sheets

U.S. PATENT DOCUMENTS

| | | |
|---|---|---|
| 2003/0118487 A1 | 6/2003 | Pressman et al. |
| 2004/0137551 A1 | 7/2004 | Markovic et al. |
| 2005/0014133 A1 | 1/2005 | Light et al. |
| 2005/0032239 A1 | 2/2005 | Katz |

OTHER PUBLICATIONS

Office Action for Australian Patent Application No. 2006325850, mailed on May 5, 2011 (3 pages).

Translation provided by Foreign Associate of Office Action for Chinese Patent Application No. 200680045287.3, mailed on Mar. 1, 2010 (5 pages).

Translation provided by Foreign Associate of Office Action for Chinese Patent Application No. 200680045287.3, mailed on Aug. 9, 2011 (7 pages).

Translation provided by Foreign Associate of Office Action for Chinese Patent Application No. 200680045287.3, mailed on Oct. 8, 2010 (6 pages).

Office Action for European Patent Application No. 06 848 603.4-2113, mailed on Feb. 17, 2010 (3 pages).

Office Action for European Patent Application No. 06 848 603.4-2113, mailed on Jul. 15, 2010 (4 pages).

Translation provided by Foreign Associate of Office Action for Taiwanese Patent Application No. 095146297, mailed on Dec. 9, 2009 (3 pages).

METHOD AND APPARATUS FOR OBTAINING ALIQUOT FROM LIQUID-BASED CYTOLOGICAL SAMPLE

RELATED APPLICATION DATA

This application is a divisional of co-pending U.S. patent application Ser. No. 11/299,394, filed Dec. 12, 2005, the priority of which is claimed under 35 U.S.C. §120, and the contents of which are incorporated herein by reference in their entirety, as though set forth in full.

FIELD OF THE INVENTION

The invention pertains to the preparation of cytological samples, and more specifically, to a method and apparatus for obtaining aliquots from cytological samples, such as fluid-based Papanicolaou ("Pap") smears.

BACKGROUND

Cytology is a branch of biology dealing with the study of the formation, structure, and function of cells. As applied in a laboratory setting, cytologists, cytotechnologists, and other medical professionals make medical diagnoses of a patient's condition based on visual examination of a sample of the patient's cells. Cytological techniques lend themselves well to the detection of abnormal cells and disease in the human body.

Cytological techniques are widely employed, because collection of cell samples for analysis is generally less invasive than traditional surgical pathological procedures such as biopsies, whereby a tissue sample is excised from the patient using specialized biopsy needles having spring loaded translatable stylets, fixed cannulae, and the like. Cell samples may be obtained from the patient by a variety of techniques including, for example, by scraping or swabbing an area, or by using a needle to aspirate body fluids from the chest cavity, bladder, spinal canal, or other appropriate area. The cell samples are subsequently transferred to a glass slide for viewing under magnification. Fixative and staining solutions may be applied to the cells on the glass slide for preserving the sample for archival purposes and for facilitating examination.

A typical cytological technique is a Papanicolaou ("Pap") smear test in which cells are scraped from a woman's cervix and analyzed in order to detect the presence of abnormal cells—a precursor to the onset of cervical cancer. In a conventional Pap smear test, the cells are smeared onto a glass slide at the physician's office, and the labeled slide is then sent off to a laboratory for analysis under a microscope by a cytotechnician. More recently, liquid-based cytological techniques have been employed, which offer new ways of collecting, storing, and analyzing the cervical cells collected during a Pap smear. Instead of smearing the cells onto a microscope slide, the physician places the collected material into a vial filled with a liquid preservation medium, such as Preserv-Cyt® transport medium, and sends the vial capped and labeled vial to a laboratory for slide preparation. During slide preparation, any unwanted material, such as bacteria, blood, mucus, or other debris, is filtered from the sample, and the remaining cells are placed onto a microscope slide as a monolayer specimen for review by a cytotechnician. In this manner, the cells are able to be more readily discerned and counted to ensure that an adequate number of cells have been evaluated. Oftentimes, slide preparation using liquid-based cytological samples is performed automatically—up to eighty slides at one time. During this automated procedure, air pressure may be used to manipulated the sample. In particular, suction is used to draw the fluid onto a cylindrical filter, and a blast of air is to transfer the cells from the filter onto the slide to create the specimen.

Whether a conventional or a fluid-based Pap smear is performed, the specimen will be classified as either normal or abnormal based on the microscopic analysis of the slide. An abnormal sample can be classified into one of the major categories defined by The Bethesda System for Reporting Cervical/Vaginal Cytologic Diagnosis, which categories include Low-Grade Squamous Intraepithelial Lesions (LSIL), High-Grade Squamous Intraepithelial Lesions (HSIL), Squamous Cell Carcinoma, Adenocarcinoma, Atypical Glandular cells of Undetermined Significance (AGUS), Adenocarcinoma in situ (AIS), and Atypical Squamous Cell (ASC), which can be further sub-divided into Atypical Squamous Cell, cannot exclude HSIL (ASC-H) and Atypical Squamous Cell of Undetermined Significance (ASC-US).

If a specimen is not classified as abnormal after analysis, the Pap smear is considered normal and the patient is returned to a routine pap screen schedule (typically, once a year). With the exception of ASC-US, if a specimen is classified into any one of these abnormal categories, the patient must undergo an inconvenient and relatively painful colposcopy and biopsy to further diagnose the presence of cancer or precancer (dysplasia). Until recently, if a specimen was classified as ASC-US, the patient had to undergo repeated Pap smears every few months in hopes of determining the nature of the abnormal cells, i.e., whether they might develop into cancerous lesions or clear up on their own. In some cases, a colposcopy and biopsy was performed.

Since 2000, a specific Human Papilloma Virus (HPV) deoxynucleic acid (DNA) test, referred to as the Hybrid Capture II HPV DNA assay, manufactured by Digene Corporation, has been used to determine whether patients, whose Pap smears have been classified as ASC-US, have HPV, the high-risk serotypes (16, 18, 31, 33, 35, 39, 45, 51, 52, 56, 58, 59, and 68) of which have been recognized as a necessary factor for the development of cervical cancer (over ninety percent of women with cervical cancer have high-risk HPV).

Based on the strong correlation between HPV and cervical cancer, it has been recommended that HPV DNA testing be used as a triage test for patients whose Pap smear results are classified as ASC-US. That is, patients who have ASC-US Pap smear results and negative HPV test results can be reassured that their short term risk of developing cervical cancer is very low, and that they could safely return to a routine Pap smear schedule. In contrast, women who have ASC-US Pap smear results and positive results for high-risk HPV should undergo the colposcopy/biopsy process in the same manner as if the Pap smear would have originally been classified as LSIL, HSIL, or any of the other abnormal categories. A recent study has shown that performing an HPV DNA test would ultimately spare forty to sixty percent of patients from undergoing a colposcopic/biopsy examination.

In the case where a conventional Pap smear has been performed, the patient will typically have to make another visit to the physician to obtain another sample for HPV DNA testing. In the case where a liquid-based Pap smear has been performed, however, the same sample used to perform the Pap smear analysis can be conveniently used to perform a "reflexive" HPV DNA test, thereby obviating the need for a repeat clinic visit and Pap smear. In this case, if a slide is positive for ASC-US, an aliquot (e.g., 4 ml) of the fluid sample is removed from the stored vial and sent to a molecular diagnostic laboratory for HPV DNA testing.

Theoretically, an HPV DNA test can be performed at any time during the Pap smear process. However, because it is currently not commercially practical to perform the HPV DNA test in conjunction with every Pap smear, the HPV DNA test is typically performed in response to a ASC-US Pap smear result. Thus, in the case of liquid-based Pap smears, the aliquot required for HPV DNA testing would have to be taken from the sample after being processed for slide preparation, which may potentially lead to molecular contamination issues, and in the case of automated Pap smear processing, aerosol cross-contamination resulting from the use of air pressure to manipulate the sample or liquid contamination resulting from the transfer of filtered solution found in the plumbing of the automated processor. Molecular contamination is not a trivial issue because the transfer of just one nucleic molecule can produce a false-positive for HPV.

Significantly, laboratories that perform HPV DNA tests are weary of molecular contamination—a well-known problem in molecular diagnostic laboratories, which typically employ special engineering and design features, laboratory practices, and monitoring activities to minimize molecular contamination in all of their activities. Because automated systems for making Pap smear slides are designed to safely and effectively handle cells—not nucleic acids, the sterilization protocols followed by technicians when operating these systems do not satisfy the strict molecular contamination control safeguards and procedures required by molecular diagnostic laboratories. Thus, due to the risk of cross-contamination, molecular diagnostic laboratories may not accept aliquots that have been taken from an already processed liquid-based Pap smear for fear of unnecessarily generating false HPV positives.

Besides being used for HPV DNA testing, aliquots from liquid-based Pap smear samples can also be used in DNA testing for other sexually transmitted diseases, such as *Chlamydia trachomatis* and *Neisseria gonorrhoeae*. However, false positives are a special problem when testing for *Chlamydia trachomatis* and *Neisseria gonorrhoeae*, because they could have enormous family and social repercussions. Thus, molecular diagnostic laboratories are even more reluctant to accept aliquots from already processed liquid-based Pap smear samples. Because testing for other sexually transmitted diseases need not be used to triage ASC-US specimens, and are intended to be performed in parallel to the Pap smear tests at the request of the physician, aliquots may be taken from the Pap smear samples prior to processing, e.g., by manually pipetting the aliquot from the vial, thereby minimizing the risk of cross-contamination. However, this step may still not satisfy the strict contamination prevention requirements imposed by molecular diagnostic laboratories.

Besides contamination issues, the pipetting of an aliquot from a fluid-based Pap smear sample, whether done before or after the sample is processed, and whether done for HPV testing or testing of any other sexually transmitted disease, increases cost in the form of manual labor (which involves not only pipetting the aliquot into an extra vial, but also labeling the vial), material costs for the pipettes and extra vials, and storage space, which when multiplied by the thousands of samples processed, becomes significant.

There thus is a need to provide an improved method and apparatus for obtaining an aliquot from a fluid-based cytological sample, such as a Pap smear sample.

SUMMARY OF THE INVENTION

In accordance with a first aspect of the present inventions, a method of processing a vial having a collection chamber containing a fluid-based cervical-vaginal sample, and an aliquot chamber, is provided. The method comprises flowing an aliquot of the sample from the collection chamber into the aliquot chamber while the sample within the collection chamber is isolated from the exterior environment. One method comprises unsealing the aliquot chamber from the collection chamber, in which case, the sample aliquot is flowed from the collection chamber into the unsealed aliquot chamber.

The method further comprises sealing the aliquot chamber from the collection chamber to isolate the aliquot sample from the remaining sample portion in the collection chamber, and transferring at least some of the remaining sample portion from the collection chamber to a microscope slide while the aliquot chamber is sealed from the collection chamber. The vial may have a vial container carrying the collection chamber and a vial cap (which may optionally carry the aliquot chamber) mated with the vial container, in which case, the method may further comprise unmating the vial cap from the vial container to expose the remaining sample portion within the collection chamber. Removal of the vial cap may expose the remaining sample portion within the collection chamber to a HPV contaminant at a molecular level. For example, if some of the remaining sample portion is automatically transferred from the collection chamber to the slide, the remaining sample portion may be exposed to the HPV contaminant when automatically transferred to the slide. However, because the aliquot sample is isolated within the aliquot chamber from the collection chamber, the aliquot sample will not be exposed to any HPV contaminant that enters the collection chamber.

The method further comprises reserving the slide for cytological screening of the sample for precursors to cervical cancer, and reserving the aliquot sample for deoxynucleic acid (DNA) testing to determine the presence of high-risk Human Papilloma Virus (HPV) in the sample. The method may optionally comprise examining the slide to cytologically screen the sample for the cervical cancer precursors, and DNA testing the aliquot sample to determine the presence of high-risk HPV in the sample. In one method, the DNA testing is only performed in response to an abnormal result of the cytological screening, e.g., an Atypical Squamous Cell of Undetermined Significance (ASC-US) result.

In accordance with a second aspect of the present inventions, another method of processing a vial having a collection chamber containing a fluid-based sample (e.g. a cervical-vaginal sample), and an aliquot chamber, is provided. The method comprises unsealing the aliquot chamber from the collection chamber, flowing an aliquot of the sample from the collection chamber into the aliquot chamber, and sealing the aliquot chamber from the collection chamber in a similar manner described above. The method further comprises removing at least some of the remaining sample portion from the collection chamber while the aliquot chamber is sealed from the collection chamber. Optionally, at least some of the remaining sample portion is transferred to a microscope slide.

Significantly, if the remaining sample portion is exposed to any cross-contaminants from another sample during removal of some of the remaining sample portion from the collection chamber, the isolated aliquot sample will not be exposed to any cross-contaminant that enters the collection chamber. Cytological examination and DNA testing can then be performed on the respective removed remaining sample portion and aliquot sample in the manner discussed above.

In accordance with a third aspect of the present inventions, a sample vial is provided. The sample vial comprises a vial container and a sample collection chamber within the vial container. The sample vial may contain a fluid-based sample (e.g., a cervical-vaginal sample) within the collection chamber. The sample vial further comprises an aliquot chamber, and a vial cap configured to be mated with the vial container to enclose the collection chamber. The vial may optionally comprise a sealed port configured to selectively provide direct access to the aliquot chamber. The aliquot chamber may abut the collection chamber, but in alternative embodiments, the aliquot chamber may be coupled to the collection chamber via an intermediate passageway. The vial further comprises a valve mechanism for selectively sealing and unsealing the aliquot chamber from the collection chamber. Although the present inventions should not be so limited in their broadest aspects, sealing and unsealing the aliquot chamber from the collection chamber allows an aliquot of a sample to be flowed from the collection chamber into the aliquot chamber and isolated from the remaining sample portion in the collection chamber. In one embodiment, the vial cap carries the aliquot chamber and the valve mechanism. In another embodiment, the vial container carries the aliquot chamber and the valve mechanism.

In one embodiment, the valve mechanism includes a valve configured to be selectively located within the aliquot chamber to prevent fluid communication between the aliquot chamber and the collection chamber, and displaced from the aliquot chamber to allow fluid communication between the aliquot chamber and the collection chamber. In another embodiment, the valve mechanism includes a valve configured to be selectively located at an interface between the aliquot chamber and the collection chamber to prevent fluid communication between the aliquot chamber and the collection chamber, and displaced from the interface to allow fluid communication between the aliquot chamber and the collection chamber.

In either case, the valve mechanism may include an actuator that can be externally manipulated to selectively seal and unseal the aliquot chamber from the collection chamber with the valve. As examples, the actuator may be configured to be rotationally translated to operably move the valve relative to the aliquot chamber (e.g., the actuator can be rotated one way to seal the aliquot chamber from the collection chamber, and rotated the other way to unseal the aliquot chamber from the collection chamber) or axially translated to operably move the valve relative to the aliquot chamber (e.g., the actuator can be pulled upward to seal the aliquot chamber from the collection chamber, and pushed downward to unseal the aliquot chamber from the collection chamber). In the latter case, a spring may be coupled to the actuator to urge the valve to seal the aliquot chamber from the collection chamber to obviate the need to pull the actuator upward.

Other and further aspects and features of the invention will be evident from reading the following detailed description of the preferred embodiments, which are intended to illustrate, not limit, the inventions.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DESCRIPTION OF ILLUSTRATED EMBODIMENTS

Figure 1:
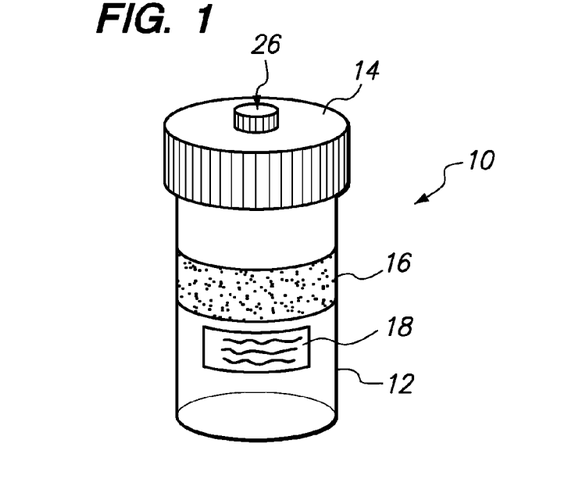
FIG. 1 is a perspective view of one embodiment of a sample vial constructed in accordance with the present invention.

Referring to FIG. 1, a sample vial 10 constructed in accordance with one embodiment of the present invention will be described. The vial 10 may be used to contain a fluid-based sample, such as a cervical-vaginal sample collected from a patient at a physician's office. The fluid-based sample typically comprises cytological material suspended in an aqueous preservative fluid.

To this end, the vial 10 comprises a hollow vial container 12 and a vial cap 14 that can be placed onto the vial container 12 to enclose a sample contained within the vial container 12. As depicted, the vial container 12 and vial cap 14 are generally cylindrical in shape. The selected size of the vial container 12 and vial cap 14 may vary, but preferably is large enough to contain the minimum amount of sample necessary to perform the intended diagnostic test. In the illustrated embodiment, the vial container 12 is capable of containing at least 20 ml of fluid, which is the minimum amount of sample required by the Food and Drug Administration (FDA) for automated transfer onto a microscope slide using Cytyc's ThinPrep® 2000 or Thinprep® 3000 slide preparation systems. For example, the vial container 12 may have an outer diameter of approximately 1 and 5/16 inches and an axial length of approximately 2 and 3/4 inches, and the vial cap 14 may have an outer diameter of approximately 1 and 9/16 inches and an axial length approximately 7/16 of an inch.

The vial container 12 is composed of a translucent or transparent material to allow a user to determine the fluid level inside of the vial 10. A suitable material is a plastic, such as polypropylene homopolymer, available under the trade designation AMOCO 4018. The vial cap 14 may be releasably mated with the vial container 12 using a standard threaded engagement (not shown), and may be composed of a plastic material, such as polypropylene random copolymer, available under the trade designation AMOCO 8949. The materials of which the vial container 12 and vial cap 14 are composed may be injection molded to rapidly and inexpensively produced the container 12 and cap 14, although other suitable manufacturing processes may be utilized depending on the particular materials selected.

A seal (not shown) may be disposed between the vial container 12 and cap 14 to form a fluid-tight seal when sufficient torque is applied to the cap 14 relative to the container 12. Sealing is important to prevent both leakage and evaporation of the preservative solution in the vial container 12, as well as to prevent the sample from being exposed to external contaminants. The seal may be composed of any material or materials capable of withstanding attack by the preservation solution in the vial container 12, which typically includes an alcohol solution, such as methanol in a buffer. Due to the low viscosity and high vapor pressure of the preservative solution, as well as the very low density and high permeability of the vapor phase thereof, a high integrity, reliable, seal composition is desired. Further, because the vial 10 may be stored for a year or more prior to use, and be subject to temperature extremes during transport and storage, the seal should be capable of retaining its sealing characteristics and structural integrity for extended periods of time without excessive loss of fluid due to evaporation. The seal material also should not degrade and contaminate the sample. In one embodiment that meets these requirements, the seal is composed of a multi-composite material, including a sufficiently thick, dense, resilient layer disposed on a vapor barrier. The resilient layer may be oriented toward the sample to provide an effective seal. The seal may include a synthetic olefin rubber or an elastomeric alloy co-extruded on a thin vapor barrier, such as that available from Tri-Seal, Inc., located in Blauvelt, N.Y., and sold under the trade name TRI SEAL SOR-117.

The vial container 12 includes a fluid level indicia 16 by which a user may determine a proper amount of preservation fluid to fill the vial 10 or that the vial 10 is filled properly prior to addition of the cytological material. The fluid level indicia 16 may be a frosted annular band of a predetermined axial length disposed about a circumference of the vial container 12 at a predetermined axial location to indicate the acceptable fill range of the vial 10, so that a proper slide sample can be prepared from the sample by an automated specimen preparation system, such as Cytyc's ThinPrep® 2000 or Thin-Prep® 3000 slide preparation systems. Alternatively, the fluid level indicia 16 may be a single fill line or an upper fill line and a lower fill line, in which case, the upper fill line indicates a maximum level to which the vial container 12 should be filled and the lower fill line indicates a minimum amount of fluid necessary to prepare a specimen from the sample.

The vial container 12 also includes sample indicia 18, which can be used to identify a patient to whom the sample corresponds, as well as a slide prepared from the sample contained in the sample vial 10. The sample indicia 18 may be machine-readable, such as a bar code, which can be ready by an automated cytological specimen preparation system, such as Cytyc's ThinPrep® 2000 or ThinPrep® 3000 slide preparation systems.

In an optional embodiment, the vial container 12 and vial cap 14 may be specially configured for automated manipulation. For example, the vial container 12 may have laterally protruding anti-rotation lugs (not shown), and the vial cap 14 may have a torque pattern of ribs (not shown), thereby allowing the cap 14 to be screwed on and screwed off of the vial container 12 using automated machinery. Additional details regarding these features are disclosed in U.S. patent application Ser. No. 09/156,952, entitled "Sample Vial for Use in Preparing Cytological Specimen," which is fully and expressly incorporated herein by reference.

Figure 2:
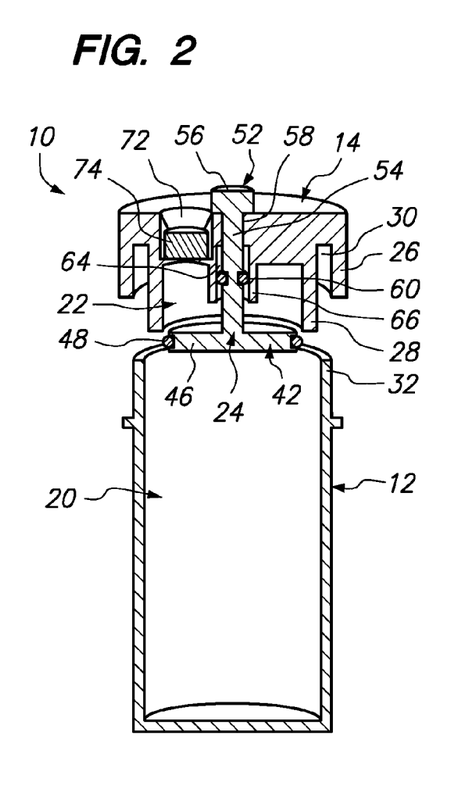
FIG. 2 is a cross-sectional exploded view of the sample vial of FIG. 1, particularly showing a valve mechanism in an open position.
Figure 3:
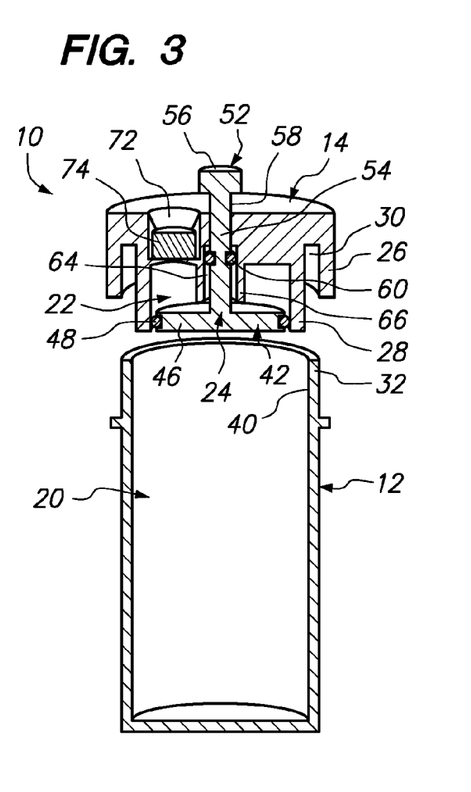
FIG. 3 is a cross-sectional exploded view of the sample vial of FIG. 1, particularly showing the valve mechanism is the closed position.

Referring further to FIGS. 2 and 3, the vial 10 includes a feature that allows an aliquot sample to be taken and isolated from the sample contained within the vial container 12. In particular, the vial 10 comprises a collection chamber 20 formed within the vial container 12 for collection of the sample, an aliquot chamber 22 for containing the aliquot sample, and a valve mechanism 24 for selectively sealing and unsealing the aliquot chamber 22 from the collection chamber 20, so the aliquot sample can be transferred from the collection chamber 20 into the aliquot chamber 22 where it can be isolated from the remaining portion of the sample within the collection chamber 20. In the illustrated embodiment, the aliquot chamber 22 abuts the collection chamber 20, although alternatively, aliquot chamber 22 may communicate with the collection chamber 20 via, e.g., a passageway.

Figure 4:
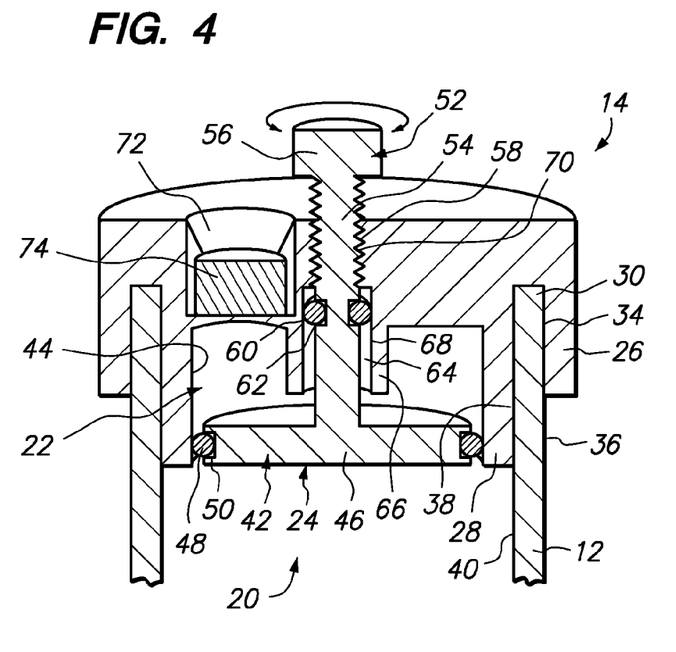
FIG. 4 is a close-up cross-sectional view of a vial cap of the sample vial of FIG. 2.

In the embodiment illustrated in FIGS. 2 and 3, the aliquot chamber 22 and valve mechanism 24 are carried by the vial cap 14. In particular, the vial cap 14 includes an outer annular flange 26, an inner annular flange 28, and an annular space 30 between the flanges 26, 28. The vial container 12 includes a lip 32 that is sized to fit within the annular space 30 of the vial cap 14 in a snug manner, so that the inner surface 34 of the outer annular flange 26 bears against the outer surface 36 of the vial container 12, and the outer surface 38 of the inner annular flange 28 bears against the inner surface 40 of the vial container 12, as best illustrated in FIG. 4. In the illustrated embodiment, the inner surface 34 of the outer annular flange 26 and the outer surface 36 of the vial container 12 include threads (not shown), so that the vial cap 14 can be firmly screwed on the vial container 12. As can seen, the inner annular flange 28 of the vial cap 14 defines the aliquot chamber 22 therein, which absent the valve mechanism 24, would normally be in fluid communication with the collection chamber 20 when the vial cap 14 is mated with the vial container 12.

The valve mechanism 24 includes a valve 42 that is configured to directly interface with the aliquot chamber 22 to allow or prevent fluid communication with the collection chamber 20. In the embodiment illustrated in FIGS. 2 and 3, the valve 42 is configured to be selectively displaced from the aliquot chamber to allow fluid communication between the aliquot chamber 22 and the collection chamber 20 (FIG. 2), and located within the aliquot chamber 22 to prevent fluid communication between the aliquot chamber 22 and the collection chamber 20 (FIG. 3).

As best shown in FIG. 4, when preventing fluid communication between the respective chambers 20, 22, the valve 42 sealingly bears against the inner surface 44 of the inner annular flange 28. To this end, the valve 42 includes an annular flange 46 that has a diameter slightly smaller than the diameter of the aliquot chamber 22 and an O-ring seal 48 seated within an annular recess 50 formed around the circumferential edge of the annular flange 46, so that the total diameter of the valve 42 is slightly greater than the diameter of the aliquot chamber 22 in order to facilitate the sealing arrangement.

The valve mechanism 24 further includes an actuator 52, which includes a shaft 54 coupled to the valve 42 and a boss 56 coupled to the end of the shaft 54 and extending up through an upper bore 58 formed in the vial cap 14. As such, the boss 56 can be externally manipulated to selectively displace the valve 42 from the aliquot chamber 22 by axially moving the actuator shaft 54 downward, and locate the valve 42 within the aliquot chamber 22 by axially moving the actuator shaft 54 upward. The annular flange 46 of the valve 42, the shaft 54, and the boss 56 may be conveniently formed from the same material as a unibody design, e.g., in an injection molding process using a plastic material, such as polypropylene or Acrylonitrile Butadiene Styrene (ABS).

As best shown in FIG. 4, in order to prevent fluid communication between the aliquot chamber 22 and the external environment that may otherwise occur through the upper bore 58, the valve mechanism 24 includes an O-ring seal 60 seated within an annular recess 62 formed around the circumference of the shaft 54. The O-ring seal 60 axially moves within an enlarged lower bore 64 between the upper bore 58 and the aliquot chamber 22. In the illustrated embodiment, the lower bore 64 is defined by an innermost annular flange 66 formed within the vial cap 14, so that the O-ring seal 60 bears against an inner surface 68 of the innermost annular flange 66. Thus, the O-ring seal 60 axially moves within the lower bore 64 in a sealing arrangement to allow the actuator shaft 54, and thus, the valve 42, to move up or down relative to aliquot chamber 22, while preventing fluid communication between the aliquot chamber 22 and the external environment through the upper bore 58.

In the embodiment illustrated in FIGS. 2 and 3, axial movement of the actuator shaft 54 is accomplished by rotationally translating the boss 56 (shown by arrow), and thus, the shaft 54, to operably move the valve 42 relative to the aliquot chamber 22. To this end, as best shown in FIG. 4, a threaded arrangement 70 is provided between the actuator shaft 54 and the upper bore 58. Thus, clockwise rotation of the boss 56 causes the shaft 54, and thus the valve 42, to move axially downward, and counterclockwise rotation of the boss 56 causes the shaft 54, and thus the valve 42, to move axially upward. As can be appreciated, the boss 56, which is larger than the shaft 54, allows the user to more easily and ergonomically rotate the shaft 54 against any frictional resistance caused by the interaction of the valve 42 and aliquot chamber 22. The boss 56 can be further provided with a knurled surface (not shown) to facilitate gripping by the user. Alternatively, rather than using a boss or any other element that protrudes from the top of the vial cap 14, a slot or other suitable pattern can be formed at the end of the shaft 54 to allow a tool, such as a screw driver, to be mated with the shaft 54 for subsequent rotation thereof.

To allow user access to the aliquot sample, the vial cap 14 includes an access port 72 adjacent the aliquot chamber 22 and a sealing mechanism in the form of septum 74 seated within the access port 72 to seal it, thereby preventing fluid communication from the aliquot chamber 22 through the access port 72 until the user is ready to remove the aliquot sample from the aliquot chamber 22 for examination. User access to the aliquot sample can be accomplished, e.g., by puncturing the septum 74 with a syringe (not shown) and drawing the aliquot sample from the chamber 22 into the syringe. Alternatively, a seal may be bonded on top surface of the vial cap 14 above the access port 72 or a screw-on plug or cap can be used to seal the access port 72.

Figure 5:
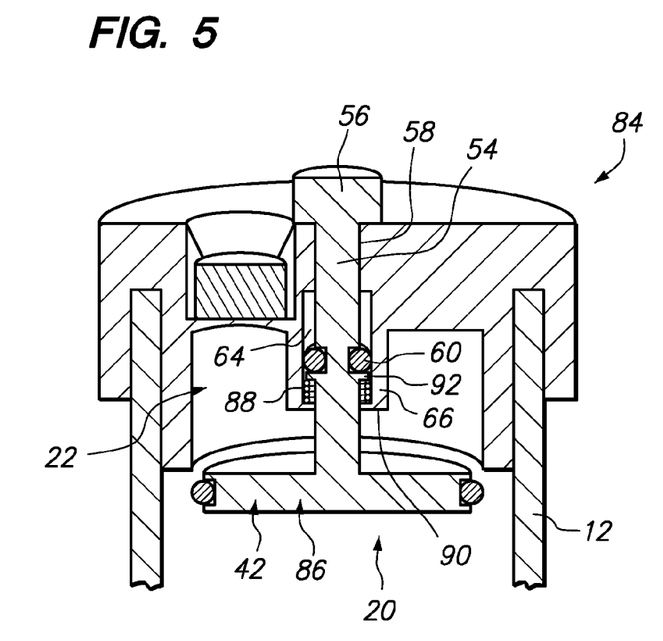
FIG. 5 is a close-up cross-sectional view of an alternative vial cap that can be used with the sample vial of FIG. 1, particularly showing a valve mechanism in an open position.
Figure 6:
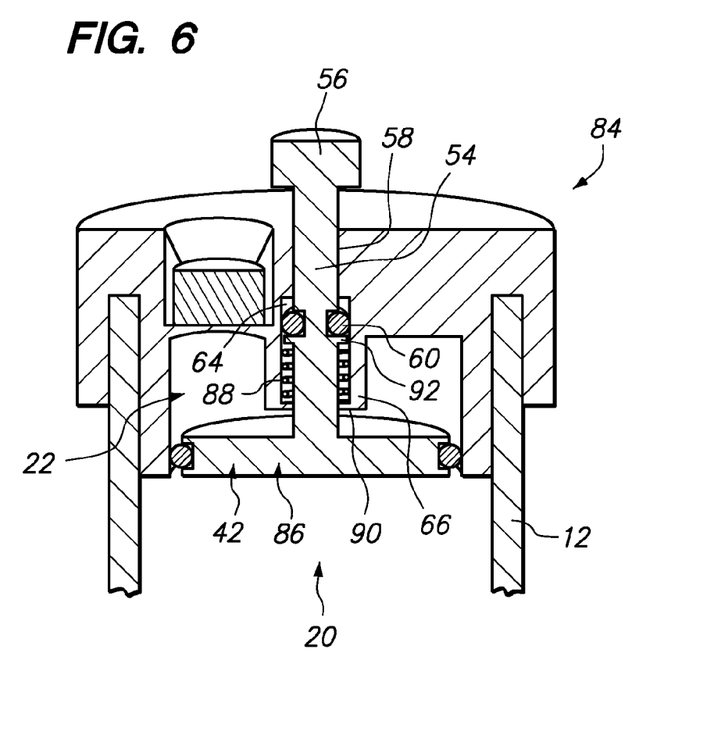
FIG. 6 is a close-up cross-sectional view of vial cap of FIG. 5, particularly showing the valve mechanism in a closed position.

Referring now to FIGS. 5 and 6, an alternative embodiment of a vial cap 84 will be described. The vial cap 84 is identical to the vial cap 14 illustrated in FIGS. 2 and 3, which the exception that it comprises a valve mechanism 86, wherein the actuator shaft 54 is configured to be only axially translated, i.e., without rotational translation. In this case, there is no threaded arrangement between the shaft 54 and the upper bore 58. Rather, the actuator shaft 54 is slidably engaged with the bore 58 in the axial direction, so that a user may simply push or pull the shaft 54 to axially move the valve 42 relative to the aliquot chamber 22. The valve mechanism 86 comprises a spring 88 disposed between an annular flange 90 inwardly extending from the innermost annular flange 66 at the bottom of the enlarged lower bore 64 and an annular flange 92 outwardly extending from the actuator shaft 54 just below the O-ring seal 60.

In this manner, the spring 88 urges the actuator shaft 54 axially upward, and thus, the valve 42 into the aliquot chamber 22. As such, absence any external force, fluid communication between the aliquot chamber 22 and the collection chamber 20 (shown in FIGS. 2 and 3) is prevented. However, when a user pushes axially downward on the boss 56, and thus the actuator shaft 54, against the urging force of the spring 88, the valve 42 is displaced from the aliquot chamber 22, thereby allowing fluid communication between the aliquot chamber 22 and the collection chamber 20 (FIG. 5). When the user releases the boss 56, and thus the shaft 54, the urging force of the spring 88 will cause the actuator shaft 54 to axially move upward, thereby moving the valve 42 back into the aliquot chamber 22 to prevent fluid communication with the collection chamber 20 (FIG. 6). In an alternative embodiment, the boss 56 is eliminated, and the user need only push down or release the top of the actuator shaft 54. The end of the actuator shaft 54 may be recessed within the vial cap 84, in which case, the user may push down on the actuator shaft 54 using a simple tool.

In the previously illustrated embodiments, the valve mechanisms selectively prevent fluid communication between the aliquot chamber 22 and collection chamber 20 by placing the valve within the aliquot chamber 22. In other embodiments, the valve mechanism may have a valve that directly interfaces with the aliquot chamber 22 in other manners to prevent such fluid communication.

Figure 7:
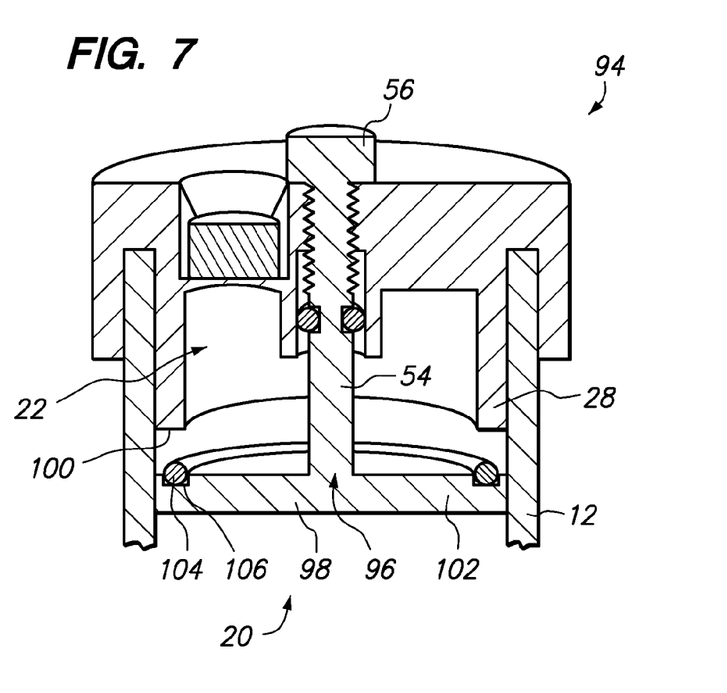
FIG. 7 is a close-up cross-sectional view of another alternative vial cap that can be used with the sample vial of FIG. 1, particularly showing a valve mechanism in an open position.
Figure 8:
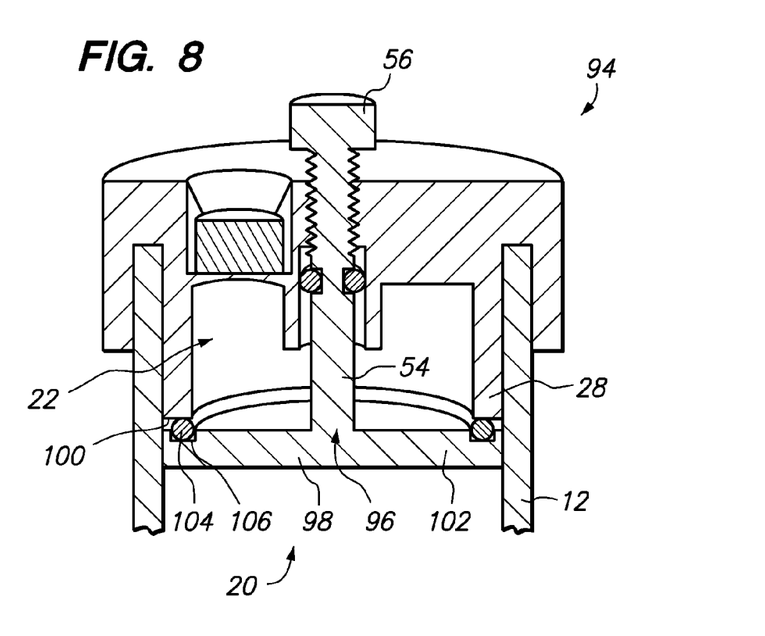
FIG. 8 is a close-up cross-sectional view of vial cap of FIG. 7, particularly showing the valve mechanism in a closed position.

For example, referring to FIGS. 7 and 8, another alternative embodiment of the vial cap 94 will be described. The vial cap 94 is identical to the vial cap 14 illustrated in FIGS. 2 and 3, with the exception that it comprises a valve mechanism 96 that seals the aliquot chamber 22 at the interface with the collection chamber 20. In particular, the valve mechanism 96 comprises a valve 98 configured to be selectively displaced from a lower-most edge 100 of the inner annular flange 28 to allow fluid communication between the aliquot chamber 22 and the collection chamber 20 (FIG. 7), and placed against the lower-most edge 100 of inner annular flange 28 to prevent fluid communication between aliquot chamber 22 and collection chamber 20 (FIG. 8).

When preventing fluid communication between the respective chambers, the valve 98 sealingly bears against the lower-most edge 100 of the inner annular flange 28. To this end, the valve 98 includes an annular flange 102 that has a diameter greater than the diameter of the aliquot chamber 22 and an O-ring seal 104 seated within an annular recess 106 within the upper surface of the flange 102, so that the O-ring seal 104 can contact the lower-most edge 100 of the inner annular flange 28 in order to facilitate the sealing arrangement.

In the same manner described above with respect to FIGS. 2 and 3, axial movement of the actuator shaft 54 is accomplished by rotationally translating the boss 56 (shown by arrow), and thus, the shaft 54, to operably move the valve 98 relative to the aliquot chamber 22. That is, clockwise rotation of the boss 56 causes the shaft 54, and thus the valve 98, to move axially downward, and counterclockwise rotation of the boss 56 causes the shaft 54, and thus the valve 98, to move axially upward. Alternatively, in the same manner described above with respect to FIGS. 5 and 6, the valve mechanism may be configured, such that the shaft 54 need only be axially translated, i.e., without rotational translation.

It should be appreciated that the incorporation of the aliquot chamber and valve assembly into the vial cap, as illustrated in FIGS. 1-8, allows the vial 10 to be stored upright in a standard manner without hindrance by any portion of the valve mechanism protruding from the vial and without risk that the remaining portion of the sample contained in the collection chamber 20 will leak into the aliquot chamber 22 with the vial 10 is stored upright. In addition, incorporation of the aliquot chamber into the vial cap provides the option of separating the vial cap containing the aliquot sample from the vial body, transferring the separated vial cap with the contained sample aliquot to a different location for molecular testing, and recapping and leaving the vial body at the cytological laboratory for producing a slide specimen or for any other reason. However, in this case where the aliquot chamber is incorporated into the vial cap, the vial 10 will need to be turned upside down to flow the sample aliquot from the collection chamber 20 into the aliquot chamber 22. In the case where an automated specimen preparation process is to be used to transfer the aliquot sample into the aliquot chamber 22, this would require an additional step of flipping the vial upside down. Also, because the aliquot sample will be subsequently tested, it is prudent that separate sample indicia (not shown) be placed on the vial cap 14 in addition to the vial container 12 to eliminate or minimize the possibility that vial caps and vial containers will be incorrectly mated together.

Figure 9:
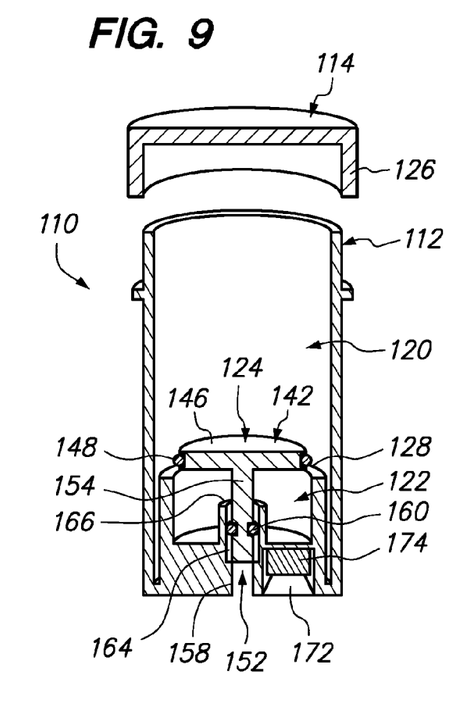
FIG. 9 is a cross-sectional exploded view of another embodiment of a sample vial constructed in accordance with the present inventions, particularly showing a valve mechanism in an open position.
Figure 10:
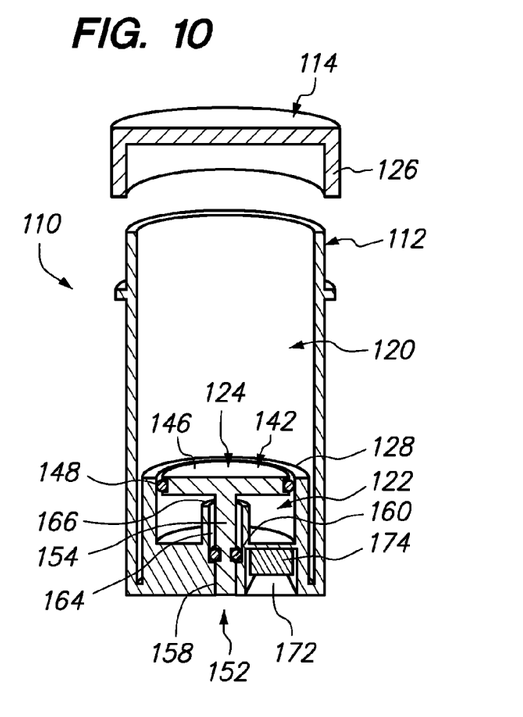
FIG. 10 is a cross-sectional exploded view of the sample vial of FIG. 9, particularly showing the valve mechanism is the closed position.

As illustrated in FIGS. 9 and 10, an embodiment of a sample vial 110, wherein the aliquot chamber and valve mechanism are integrated into the vial container, will now be described. In this case, the vial 110 need not be turned upside down to flow the sample aliquot from the collection chamber into the aliquot chamber, and because the aliquot chamber is not incorporated into the vial cap, separate sample indicia is not required for the vial cap. In particular, the vial 110 comprises a hollow vial container 112 and a vial cap 114 that can be placed onto the vial container 112 to enclose a sample contained within the vial container 112. The vial container 112 and vial cap 114 are identical to the vial container 12 and vial cap 14 illustrated in FIGS. 1-3 in all respects, with the following exceptions.

Because the vial cap 114 does not carry an aliquot chamber and valve mechanism, the vial cap 114 may be a standard vial with includes a single annular flange 126 for mating with the top of the vial container 112. Like the vial 110 illustrated in FIGS. 2 and 3, the vial 110 comprises a collection chamber 120 formed within the vial container 112 for collection of the sample, an aliquot chamber 122 for containing the aliquot sample, and a valve mechanism 124 for selectively sealing and unsealing the aliquot chamber 122 from the collection chamber 120, so the aliquot sample can be transferred from the collection chamber 120 into the aliquot chamber 122 where it can be isolated from the remaining portion of the sample within the collection chamber 120. However, unlike the vial illustrated in FIGS. 2 and 3, the aliquot chamber 122 and valve mechanism 124 are carried by the vial container 112.

In particular, an annular flange 128 is formed at the bottom of the vial container 112 to define the aliquot chamber 122, which absent the valve mechanism 124, would normally be in fluid communication with the collection chamber 120. The valve mechanism 124 includes a valve 142 that is configured to directly interface with the aliquot chamber 122 to allow or prevent fluid communication with the collection chamber 120. In the embodiment illustrated in FIGS. 9 and 10, the valve 142 is configured to be selectively displaced from the aliquot chamber to allow fluid communication between the aliquot chamber 122 and the collection chamber 120 (FIG. 9), and located within the aliquot chamber 122 to prevent fluid communication between the aliquot chamber 122 and the collection chamber 120 (FIG. 10).

Figure 11:
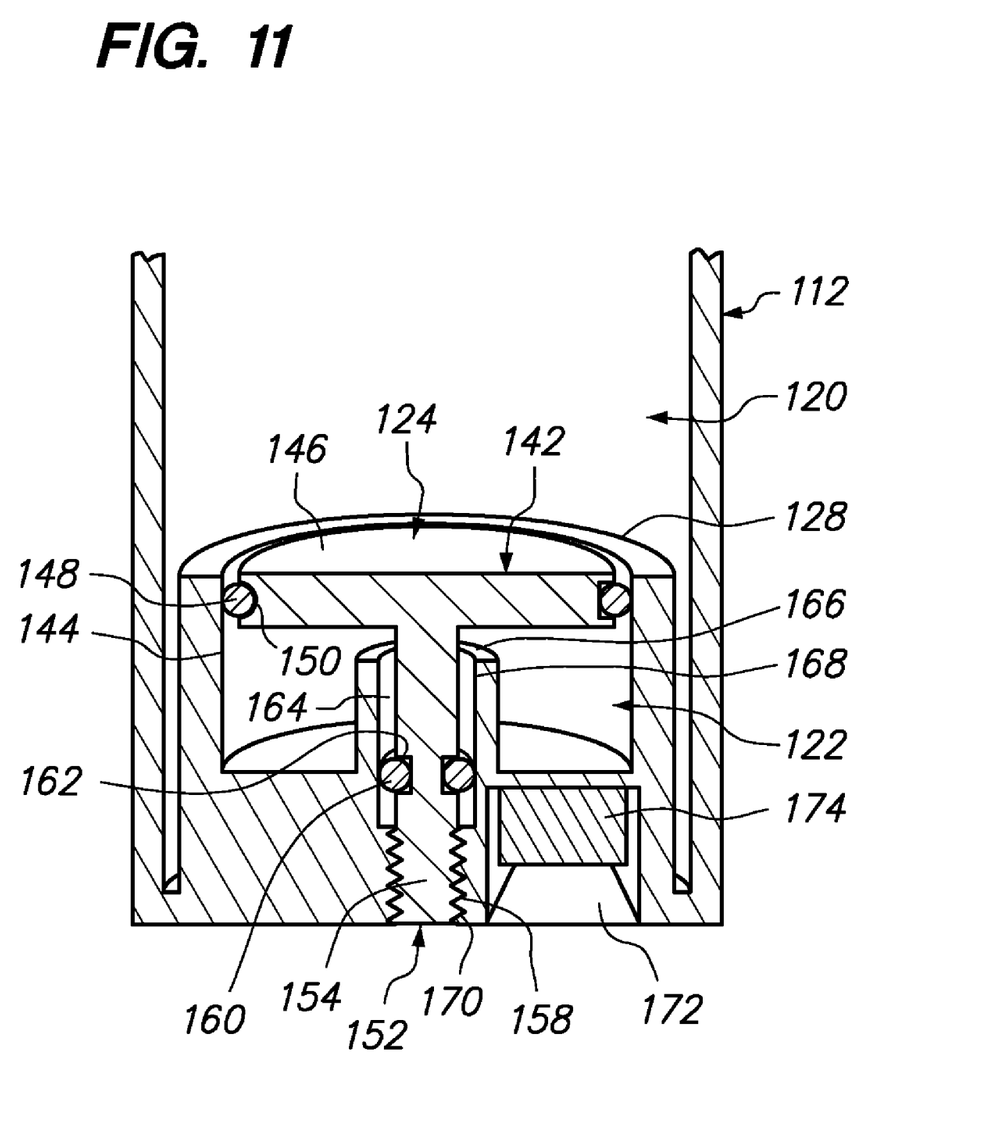
FIG. 11 is a close-up cross-sectional view of a vial cap of the sample vial of FIG. 10.

The valve 142 interfaces with the annular flange 128 in the same manner as the valve 42 interfaces with the inner annular flange 28 of the vial cap 14 illustrated in FIGS. 2 and 3. That is, as best shown in FIG. 11, when preventing fluid communication between the respective chambers, the valve 142 sealingly bears against the inner surface 144 of the annular flange 128. The valve 142 includes an annular flange 146 that has a diameter slightly smaller than the diameter of the aliquot chamber 122 and an O-ring seal 148 seated within an annular recess 150 formed around the circumferential edge of the flange 146, so that the total diameter of the valve 142 is slightly greater than the diameter of the aliquot chamber 122 in order to facilitate the sealing arrangement.

Notably, because the annular flange 128 is set off from the outer wall of the vial container 112, the risk of interfering with the sealing relationship between the valve 142 and the inner surface 144 of the annular flange 128 is minimized. That is, if an inner annular flange is not used, and instead, the valve 142 sealingly interfaces with the inner surface of the outer wall of the vial container, the act of simply grasping the vial container may warp the outer wall, thereby breaking the sealing relationship between the valve 142 and outer wall. Alternatively, if the outer wall of the vial container 112 is sturdy enough, the valve 142 could be made to interface with the inner surface of the outer wall without risk of interfering with the sealing relationship.

The valve mechanism 124 further includes an actuator 152, which includes a shaft 154 coupled to the valve 142 and extending through a lower bore 158 formed at the bottom of the vial container 112. Unlike the actuator 52 illustrated in FIGS. 2 and 3, the actuator 152 does not include a boss or any part that protrudes from the vial container, so that the bottom surface of the vial 110 is flush or recessed to facilitate the storage of the vial 110 in an upright manner. Instead, the shaft 154 is configured, such that a tool can be used to externally manipulate the valve mechanism 124 to selectively locate the valve 142 within the aliquot chamber 122 and displace the valve 142 from the aliquot chamber 122, as will be described in further detail below. The annular flange 146 of the valve 142 and the shaft 154 may be conveniently formed from the same material as a unibody design, e.g., in an injection molding process using a plastic material, such as polypropylene.

As best shown in FIG. 11, in order to prevent fluid communication between the aliquot chamber 122 and the external environment that may otherwise occur through the lower bore 158, the valve mechanism 124 includes an O-ring seal 160 seated within an annular recess 162 formed around the circumference of the shaft 154. The O-ring seal 160 axially moves within an enlarged upper bore 164 between the lower bore 158 and the aliquot chamber 122. In the illustrated embodiment, the upper bore 164 is defined by an inner annular flange 166 formed within vial container 112, so that the O-ring seal 160 bears against an inner surface 168 of the inner annular flange 166. Thus, the O-ring seal 160 axially moves within the upper bore 164 in a sealing arrangement to allow the actuator shaft 154, and thus, the valve 142, to move up or down relative to aliquot chamber 122, while preventing fluid communication between the aliquot chamber 122 and the external environment through the lower bore 158.

In the embodiment illustrated in FIGS. 9 and 10, axial movement of the actuator shaft 154 is accomplished in the same manner as the actuator shaft 54 described with respect to FIGS. 2 and 3. That is, the actuator shaft 154 may be rotationally translated to operably move the valve 142 relative to the aliquot chamber 122. To this end, a threaded arrangement 170 is provided between the actuator shaft 154 and the upper bore 158. Thus, clockwise rotation of the shaft 154 causes the valve 142 to move axially upward, and counterclockwise rotation of the shaft 154 causes the valve 142 to move axially downward. A slot or other suitable pattern is formed at the end of the shaft 154 to allow a tool, such as a screw driver, to be mated with the shaft 154 for subsequent rotation thereof.

Alternatively, in the same manner described above with respect to FIGS. 5 and 6, the valve mechanism may be configured, such that the shaft 154 need only be axially translated, i.e., without rotational translation. Or, in the same manner described above with respect to FIGS. 7 and 8, the valve mechanism may be configured, such that the valve seals the aliquot chamber 122 at the interface with the collection chamber 120, e.g., creating a seal between the upper-most edge of the inner annular flange 128 and a valve.

To allow user access to the aliquot sample, the vial container 112 includes an access port 172 adjacent the aliquot chamber 122 and a sealing mechanism in the form of septum 174 seated within the access port 172 to seal it, thereby preventing fluid communication from the aliquot chamber 122 through the access port 172 until the user is ready to remove the aliquot sample from the aliquot chamber 122 for examination. User access to the aliquot sample can be accomplished, e.g., by puncturing the septum 174 with a syringe and drawing the aliquot sample from the aliquot chamber 122 into the syringe. Alternatively, a seal may be bonded on top surface of the vial cap 114 above the access port 172 or a screw-on plug or cap can be used to seal the access port 172.

Figure 12:
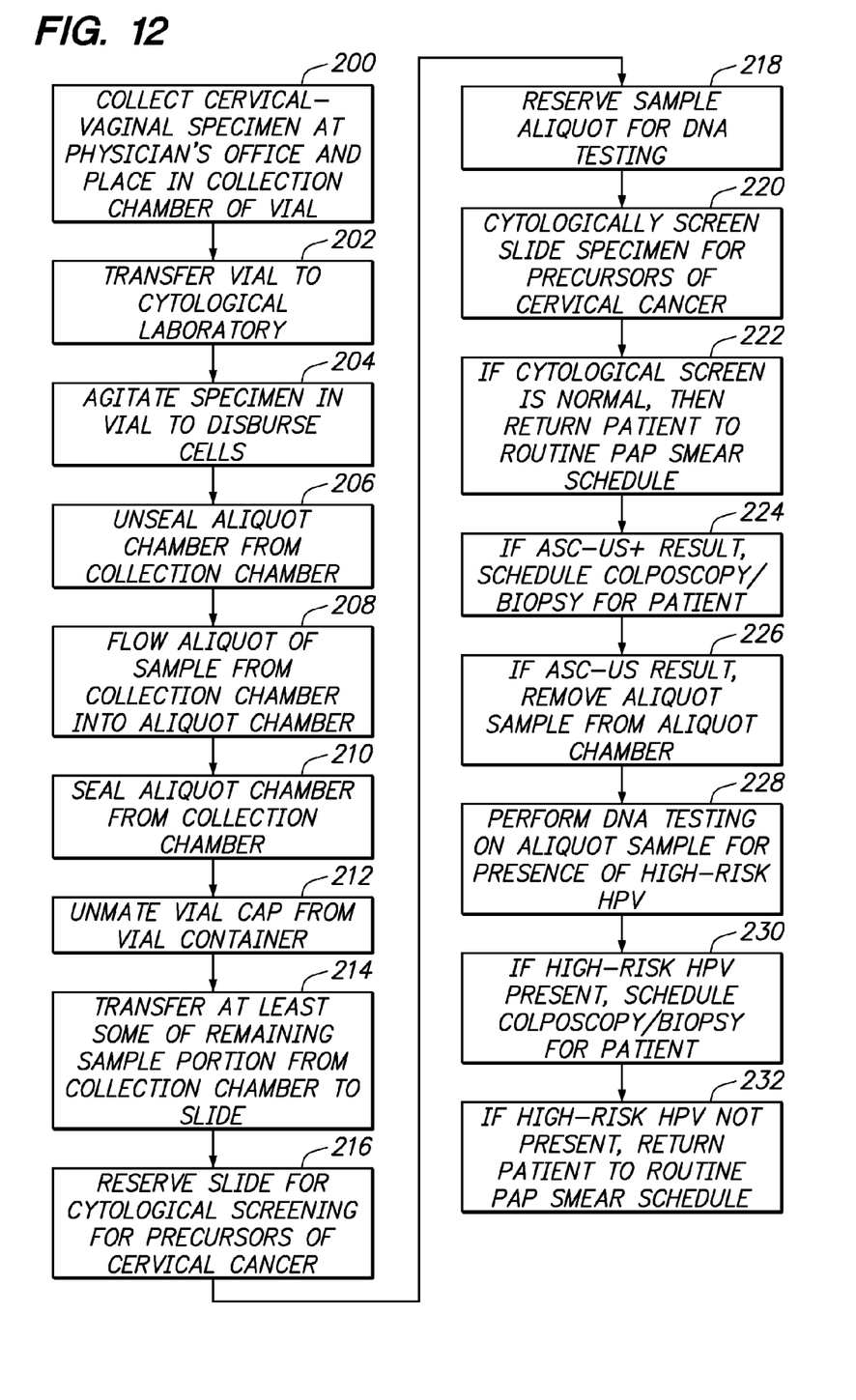
FIG. 12 is a flow diagram of a method for processing the foregoing sample vials.

Having described the structure and function of several embodiments of vials, a method of processing a vial will now be described with reference to FIG. 12. The illustrated method will be described in the context of triaging patients for precursors of cervical cancer.

First, the vial cap is removed from the vial container and a fluid-based cervical-vaginal sample is placed within the collection chamber of the vial container (step 200). This step can typically be accomplished at the physician's office. In the illustrated method, the cervical-vaginal sample taken as part of the routine Pap smear. In particular, cells are scraped from the cervix of the patient and mixed into a preservative solution, such as PreservCyt® transport medium, contained within the collection chamber of the vial container. Next, the vial cap is placed back on the vial container, and the vial with the collected fluid-based sample, is transferred to a cytological laboratory (step 202).

At the cytological laboratory, the fluid-based sample is agitated to disburse the cells (step 204), and the aliquot chamber in the vial is unsealed from the collection chamber while the vial cap is mated with the vial container (step 206). In the embodiments illustrated in FIGS. 2 and 3, this is accomplished by rotating the boss 56 on the vial cap 14 in the clockwise direction to displace the valve 42 out of the aliquot chamber 22. In the embodiment illustrated in FIGS. 5 and 6, this is accomplished by pushing the boss 56 on the vial cap 84 downward against the urging force of the spring 88 to displace the valve 42 out of the aliquot chamber 22. In the embodiment illustrated in FIGS. 7 and 8, this is accomplished by rotating the boss 56 on the vial cap 94 in the clockwise direction to displace the valve 98 away from the lower-most edge 100 of the inner annular flange 28. In the embodiment illustrated in FIGS. 9 and 10, this is accomplished by rotating the shaft 154 in the clockwise direction with the special tool to displace the valve 142 out of the aliquot chamber 122.

Next, an aliquot of the sample is flowed from the collection chamber into the unsealed aliquot chamber while the sample is isolated from an environment exterior to the vial (i.e., while the vial cap is mated with the vial container) (step 208). In vials wherein the aliquot chamber is integrated into the vial cap, such as the embodiments illustrated in FIGS. 2 and 3, FIGS. 5 and 6, and FIGS. 7 and 8, and FIGS. 9 and 10, this can be accomplished by flipping the vials upside down. In vials wherein the aliquot chamber is integrated into the vial container, such as the embodiment illustrated in FIGS. 9 and 10, the aliquot of the sample will flow from the collection chamber into the aliquot chamber in response to unsealing the aliquot chamber from the collection chamber in step 204.

Alternatively, if screw-type valve mechanisms are used, such as those illustrated in FIGS. 2 and 3, FIGS. 7 and 8, and FIGS. 9 and 10, the agitation, unsealing, and flowing steps 204, 206, 208 can be performed at the physician's office prior to transferring the respective vial to the cytological laboratory.

Next, the aliquot chamber is sealed from the collection chamber to isolate the aliquot chamber from the remaining portion of the sample contained in the collection chamber (step 210). In the embodiments illustrated in FIGS. 2 and 3, this is accomplished by rotating the boss 56 on the vial cap 14 in the counterclockwise direction to relocate the valve 42 into the aliquot chamber 22. In the embodiment illustrated in FIGS. 5 and 6, this is accomplished simply be relieving downward pressure from the boss 56 on the vial cap 84, and allowing the urging force of the spring 88 to move the valve 42 back into the aliquot chamber 22. In the embodiment illustrated in FIGS. 7 and 8, this is accomplished by rotating the boss 56 on the vial cap 94 in the counterclockwise direction to abut the valve 98 against the lower-most edge 100 of the inner annular flange 28. In the embodiment illustrated in FIGS. 9 and 10, this is accomplished by rotating the shaft 154 in the counterclockwise direction with the special tool to relocate the valve 142 into the aliquot chamber 122.

Next, the vial cap is unmated from the vial container to expose, and thereby provide access, to the remaining sample portion in the collection chamber (step 212), and at least some of the remaining sample portion is transferred from the collection chamber to a microscope slide while the aliquot chamber is sealed from the collection chamber (step 214). Typically, exposing the collection chamber to the external environment may expose the remaining sample portion to contaminants (e.g., HPV) at the molecular level. This may be especially true if the slide preparation process is performed by an automated specimen preparation system where molecular contaminants are often found. Without taking additional precautions, such molecular contaminants can be found in an aerosol or within filtered cell solution in the plumbing of the automated specimen preparation system where it can be transferred from vial to vial. However, because the aliquot sample in the aliquot chamber is isolated from the collection chamber, it will not be exposed to any contaminants that may enter the collection chamber.

Next, the slide specimen is reserved for cytological screening of the sample for precursors of cervical cancers (step 216), and the sample aliquot is reserved for DNA testing, e.g., for the present of high-risk HPV in the sample (step 218). Next, the slide is cytological screened, e.g., for precursors of cervical cancers (step 220). This can be accomplished in the same laboratory at which the slide was prepared, or alternatively, can be transferred to another laboratory. In the case where no abnormal cells are found, the patient is returned to a routine Pap smear schedule (step 222). In the case of an ASC-US+ result, the patient is scheduled for a colposcopy/biopsy at the physician's office (step 224). In the case of an ASC-US result, the aliquot sample is removed from the aliquot chamber via the access port within the vial cap or vial container (step 226), and a reflex DNA test is performed on the aliquot sample reserved in step 218 for the presence of high-risk HPV (step 228). This can be accomplished using Digene's Hybrid Capture II HPV DNA assay. If the presence of high-risk HPV is detected in the sample, the patient is scheduled for a colposcopy/biopsy at the physician's office (step 230), or alternatively may be placed on a schedule with increased Pap smear intervals. If the presence of high-risk HPV is not detected in the sample, the patient may then be returned to a routine Pap smear schedule (step 232). Optionally, other DNA tests, e.g., to detect the presence of such as *Chlamydia trachomatis* and *Neisseria gonorrhoeae*, may be performed. These other DNA tests, or even the HPV DNA test, can be alternatively performed in parallel with the cytological screening of the slide.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A biological specimen sample vial, comprising:
    a vial container comprising a sample collection chamber for holding a fluid-based biological specimen sample;
    a vial cap configured to be mated with the vial container to enclose the collection chamber;
    an aliquot chamber; and
    a valve mechanism that comprises an actuator disposed on an external surface of the sample vial, and comprises or is coupled to a wall of the aliquot chamber, the valve mechanism biased to seal the aliquot chamber from the collection chamber unless actively actuated, wherein actuating the valve mechanism unseals the aliquot chamber from the collection chamber allowing an aliquot of the sample to flow from the collection chamber into the aliquot chamber while the collection chamber is isolated from an environment exterior to the vial, and wherein terminating active actuation of the valve mechanism causes the valve mechanism to automatically seal the aliquot chamber from the collection chamber to isolate the aliquot sample from a remaining portion of the sample in the collection chamber,
    the sample vial configured such that specimen sample fluid may be removed from the sample collection chamber while the aliquot chamber is sealed from the collection chamber.

2. The sample vial of claim 1, wherein the vial cap comprises the aliquot chamber and valve mechanism.

3. The sample vial of claim 1, wherein the vial container comprises the aliquot chamber and valve mechanism.

4. The sample vial of claim 1, wherein the aliquot chamber abuts the collection chamber.

5. The sample vial of claim 1, wherein the valve mechanism includes a valve configured to be selectively located within the aliquot chamber to prevent fluid communication between the aliquot chamber and the collection chamber, and displaced from the aliquot chamber to allow fluid communication between the aliquot chamber and the collection chamber.

6. The sample vial of claim 5, wherein the valve mechanism includes a valve configured to be selectively located at an interface between the aliquot chamber and the collection chamber to prevent fluid communication between the aliquot chamber and the collection chamber, and displaced from the interface to allow fluid communication between the aliquot chamber and the collection chamber.

7. The sample vial of claim 1, wherein the actuator is configured to be rotationally translated to operably move the valve relative to the aliquot chamber.

8. The sample vial of claim 1, wherein the actuator is configured to be axially translated to operably move the valve relative to the aliquot chamber.

9. The sample vial of claim 8, further comprising a spring coupled to the actuator to urge the valve to seal the aliquot chamber from the collection chamber.

10. The sample vial of claim 8, further comprising a sealed port configured to selectively provide direct access to the aliquot chamber.

11. The sample vial of claim 1, further comprising a fluid-based, cervical-vaginal sample contained within the collection chamber.

* * * * *